(12) United States Patent
Mancosky et al.

(10) Patent No.: US 8,430,968 B2
(45) Date of Patent: Apr. 30, 2013

(54) METHOD OF EXTRACTING STARCHES AND SUGAR FROM BIOLOGICAL MATERIAL USING CONTROLLED CAVITATION

(75) Inventors: Douglas G. Mancosky, White, GA (US); Bijan Kazem, Alpharetta, GA (US)

(73) Assignee: Hydro Dynamics, Inc., Rome, GA (US)

( * ) Notice: Subject to any disclaimer, the term of this patent is extended or adjusted under 35 U.S.C. 154(b) by 701 days.

(21) Appl. No.: 12/357,465

(22) Filed: Jan. 22, 2009

(65) Prior Publication Data

US 2009/0186383 A1 Jul. 23, 2009

Related U.S. Application Data

(60) Provisional application No. 61/011,864, filed on Jan. 22, 2008.

(51) Int. Cl.
*C08B 30/00* (2006.01)
*D21C 1/02* (2006.01)

(52) U.S. Cl.
USPC .............................................. 127/34; 162/50

(58) Field of Classification Search ........................ None
See application file for complete search history.

(56) References Cited

U.S. PATENT DOCUMENTS

| | | | |
|---|---|---|---|
| 1,516,090 A | 11/1924 | Gary et al. | |
| 1,758,207 A | 5/1930 | Walker | |
| 2,907,455 A | 10/1959 | Sasaki | |
| 3,195,867 A | 7/1965 | Mould, Jr. | |
| 3,198,191 A | 8/1965 | Wyszomirski | |
| 3,663,117 A | 5/1972 | Warren | |
| 3,834,982 A | 9/1974 | Alexandrovich et al. | |
| 3,873,414 A | 3/1975 | Rocher et al. | |
| 3,920,534 A | 11/1975 | Jensen et al. | |
| 3,948,489 A | 4/1976 | Sawyer | |
| 3,954,589 A | 5/1976 | Aber et al. | |
| 3,961,776 A | 6/1976 | Sperrle | |
| 4,075,248 A | 2/1978 | Marshall et al. | |
| 4,137,159 A | 1/1979 | Sawyer | |
| 4,154,623 A * | 5/1979 | Schwengers et al. | 127/39 |
| 4,168,295 A | 9/1979 | Sawyer | |
| 4,273,075 A | 6/1981 | Freihage | |
| 4,357,931 A | 11/1982 | Wolpert et al. | |
| 4,369,100 A | 1/1983 | Sawyer | |
| 4,490,049 A | 12/1984 | Sanders et al. | |
| 4,619,733 A | 10/1986 | Kooi | |
| 4,687,549 A | 8/1987 | Kallmes | |
| 4,781,151 A | 11/1988 | Wolpert et al. | |
| 4,906,387 A | 3/1990 | Pisani | |
| 4,978,426 A | 12/1990 | Lowry | |
| 4,990,260 A | 2/1991 | Pisani | |
| 4,993,947 A | 2/1991 | Grosrey | |
| 5,082,526 A | 1/1992 | Dorris | |
| 5,085,734 A | 2/1992 | Griggs | |
| 5,116,227 A | 5/1992 | Levy | |
| 5,133,932 A | 7/1992 | Gunn et al. | |
| 5,141,328 A | 8/1992 | Dilley | |
| 5,143,699 A | 9/1992 | Herter | |
| 5,173,049 A | 12/1992 | Levy | |
| 5,173,153 A | 12/1992 | Terrett et al. | |
| 5,188,090 A | 2/1993 | Griggs | |
| 5,190,669 A | 3/1993 | Weibel | |
| 5,211,811 A | 5/1993 | Griggs et al. | |
| 5,217,574 A | 6/1993 | Griggs | |
| 5,218,984 A | 6/1993 | Allen | |
| 5,236,726 A | 8/1993 | Lancaster | |
| 5,285,443 A | 2/1994 | Patsiokas et al. | |
| 5,296,099 A | 3/1994 | Griggs et al. | |
| 5,385,298 A | 1/1995 | Griggs | |
| 5,490,727 A | 2/1996 | Poschl | |
| 5,494,748 A | 2/1996 | Spehner | |
| 5,519,670 A | 5/1996 | Walter | |
| 5,525,195 A | 6/1996 | Friend et al. | |
| 5,534,118 A | 7/1996 | McCutchen | |
| 5,538,594 A | 7/1996 | Hank et al. | |
| 5,552,133 A | 9/1996 | Lambert et al. | |
| 5,569,180 A | 10/1996 | Spears | |
| 5,605,567 A | 2/1997 | Lancaster | |
| 5,685,342 A | 11/1997 | Ekholm | |
| 5,735,934 A | 4/1998 | Spears | |

(Continued)

FOREIGN PATENT DOCUMENTS

| CA | 2115383 | 8/1994 |
|---|---|---|
| DE | 2323751 | 11/1974 |

(Continued)

OTHER PUBLICATIONS

Ladisch et al., A solvent partition method for microscale ganglioside purification. Analytical Biochemistry 146:220-231, 1985.*

(Continued)

*Primary Examiner* — Ruixiang Li
(74) *Attorney, Agent, or Firm* — Womble Carlyle Sandridge & Rice, LLP

(57) ABSTRACT

A method of extracting sugar, starch, and/or carbohydrates from feed material such as corn or corn stover is disclosed. The feed material is mixed with liquid and perhaps accelerants to form a mixture. The mixture is pumped through a controlled cavitation reactor, where it is exposed to shockwaves from cavitation events. The shockwaves open pores in the feed material and force liquid in and out of the pores to liberate trapped sugars and starches, which are dissolved in the liquid for subsequent removal.

21 Claims, 3 Drawing Sheets

U.S. PATENT DOCUMENTS

| | | | |
|---|---|---|---|
| 5,782,556 A | 7/1998 | Chu | |
| 5,810,052 A | 9/1998 | Kozyuk | |
| 5,937,906 A | 8/1999 | Kozyuk | |
| 5,957,122 A | 9/1999 | Griggs | |
| 5,964,983 A | 10/1999 | Dinand et al. | |
| 6,030,221 A | 2/2000 | Jones et al. | |
| 6,074,527 A | 6/2000 | Hsu et al. | |
| 6,074,554 A | 6/2000 | Ray et al. | |
| 6,162,767 A | 12/2000 | Adam | |
| 6,250,791 B1 | 6/2001 | Schneider | |
| 6,365,555 B1 | 4/2002 | Moser et al. | |
| 6,386,751 B1 | 5/2002 | Wootan et al. | |
| 6,454,900 B2 | 9/2002 | Bokstrom et al. | |
| 6,502,980 B1 | 1/2003 | Ekstrom et al. | |
| 6,540,922 B1 | 4/2003 | Cordemans et al. | |
| 6,576,201 B1 | 6/2003 | Woo et al. | |
| 6,627,784 B2 * | 9/2003 | Hudson et al. | 588/320 |
| 6,691,358 B1 | 2/2004 | Engstrom et al. | |
| 6,719,880 B2 | 4/2004 | Speaks et al. | |
| 7,316,501 B2 | 1/2008 | Thoma | |
| 7,360,755 B2 | 4/2008 | Hudson et al. | |
| 7,507,014 B1 | 3/2009 | League et al. | |
| 7,771,582 B2 | 8/2010 | Kazem | |
| 2002/0077373 A1 | 6/2002 | Hudson et al. | |
| 2003/0042126 A1 | 3/2003 | Nguyen et al. | |
| 2003/0057163 A1 | 3/2003 | Wood | |
| 2004/0126273 A1 | 7/2004 | Forney et al. | |
| 2004/0232006 A1 | 11/2004 | Kazem | |
| 2005/0042129 A1 | 2/2005 | Kazem | |
| 2005/0150618 A1 * | 7/2005 | Kazem et al. | 162/50 |
| 2006/0126428 A1 | 6/2006 | Hudson et al. | |

FOREIGN PATENT DOCUMENTS

| | | |
|---|---|---|
| DE | 3327137 | 2/1984 |
| DE | 10015144 | 10/2001 |
| EP | 0610914 | 8/1994 |
| EP | 0680779 | 11/1995 |
| GB | 2176535 | 12/1986 |
| JP | 48-61704 | 8/1973 |
| JP | 55139891 | 1/1980 |
| JP | 55102491 | 8/1980 |
| JP | 56045791 | 4/1981 |
| JP | 56152789 | 11/1981 |
| JP | 57111388 | 7/1982 |
| JP | 60008391 | 1/1985 |
| JP | 60226594 | 11/1985 |
| JP | 62213895 | 9/1987 |
| JP | 6039262 | 2/1994 |
| JP | 08218291 | 8/1996 |
| SU | 1694196 | 11/1991 |
| WO | WO 94/11096 | 5/1994 |
| WO | WO 00/04932 | 2/2000 |
| WO | WO 00/54818 | 11/2000 |
| WO | WO 01/87471 | 11/2001 |
| WO | WO 2004/022838 | 3/2004 |
| WO | WO 2004/103911 | 12/2004 |

OTHER PUBLICATIONS

Military Support Transp. Acad, "General Purpose Decontaiminator of Liq.—Consists of Electrode Chamber with Pulsed Current Generating Extremely High Pressure, and Cavitation", XP002298878, Derwent Publications Ltd., London, GB, Section Ch, Week 199523 (Abstract).

"Einsatz von Ultraschall zum Schadstoffabbau in Wasser: Aquasonolyse—Eine Ubersicht", Lifka J. et al., XP002298730, Chemie Ingenieur Technik, vol. 74, No. 4, pp. 403-413, Weinheim, DE.

* cited by examiner

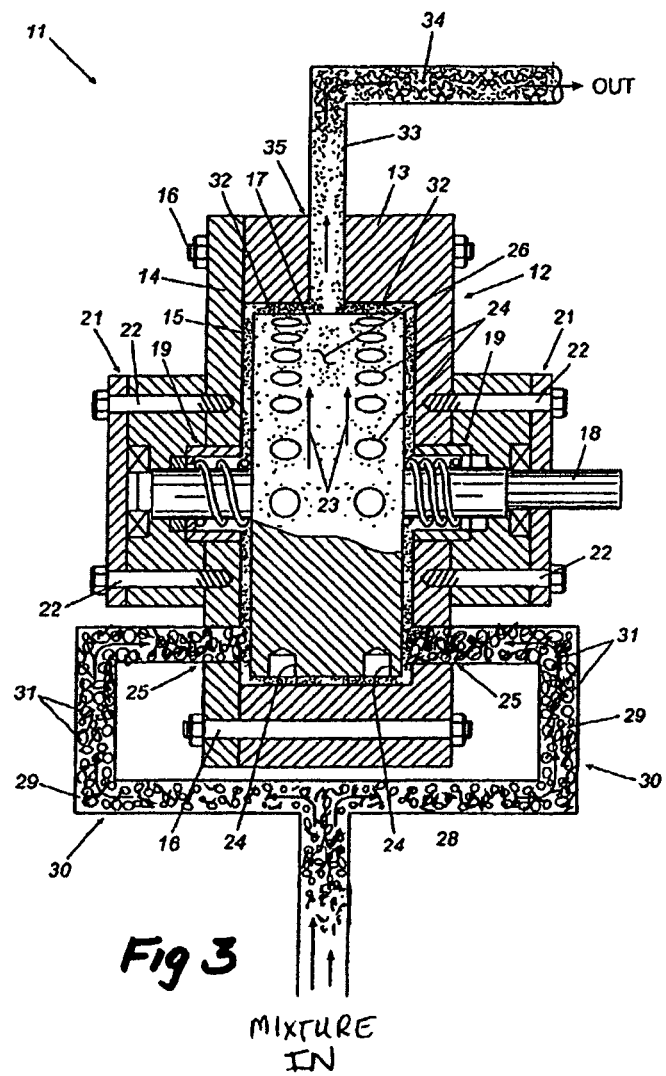

METHOD OF EXTRACTING STARCHES AND SUGAR FROM BIOLOGICAL MATERIAL USING CONTROLLED CAVITATION

REFERENCE TO RELATED APPLICATION

Priority is hereby claimed to the filing date of U.S. provisional patent application Ser. No. 61/011,864 filed on Jan. 22, 2008, the disclosure of which is incorporated fully by reference.

TECHNICAL FIELD

This disclosure relates generally to the extraction of sugars and starches from biological material and more particularly to subjecting a mixture containing biological material to controlled cavitation to enhance such extraction.

BACKGROUND

In the ethanol industry, sugars and/or starches and/or carbohydrates are extracted from biological materials such as corn, grasses, switch grass, corn stover, or other lignocellulosic biomass containing sugars and/or starches. The extracted sugars and/or starches are then fermented to convert them to ethanol, and the mixture may be distilled to remove the ethanol. Historically, sugars and starches have been extracted by soaking biological materials, such as corn, in a mixture of water and perhaps a substance to help leach out the sugars and starches such as an acid, a caustic, enzymes, and the like. The more material that can be extracted or leached, the higher the yield for a given amount of biological material. There is a need for a more efficient method of extracting or leaching sugars and/or starches and/or carbohydrates from biological feed materials that produces higher yields. It is to the provision of such a method and an apparatus for carrying out the method that the present invention is primarily directed.

SUMMARY

Briefly described, a method of extracting sugars and/or starches and/or carbohydrates from biological feed materials is disclosed. The method comprises providing a controlled cavitation reactor such as that disclosed in U. S. Pat. No. 6,627,784, the disclosure of which is incorporated by reference. The reactor generally comprises a housing defining an internal cylindrical chamber and a cylindrical rotor rotatably mounted in the chamber. The rotor has a peripheral surface spaced from a cylindrical peripheral wall of the chamber to define a cavitation zone. A plurality of bores are formed in the peripheral surface of the rotor and these bores induce cavitation within them, which projects shockwaves into and through the cavitation zone when the rotor is rotated by an external motor. The method further comprises pumping through the cavitation zone a mixture of water and biological feed material containing sugars and/or starches and/or carbohydrates to be extracted. Catalysts or accelerants such as an acid, a caustic, and enzyme, or the like may be included in the mixture. While the mixture resides in the cavitation zone, the cavitation events occurring within the bores of the rotating rotor induce relatively large shockwaves and ultrasonic pressures within the mixture. This, in turn, opens the pores in the biological material and also moves liquids and accelerants within the mixture into and out of the pores. The trapped sugars, starches, and/or carbohydrates are thereby liberated and extracted from the biological material generally faster and more efficiently than with prior art soaking and mixing techniques. The reactor can be inserted in-line as a side stream of an already existing batch extraction process or can be the primary component of a continuous process unassociated with a traditional batch process. The reaction or extraction time per volume of mixture stays the same or is reduced. Therefore, an improved and more efficient method of extracting sugars, starches, and/or carbohydrates from biological feed material such as corn is disclosed. A better understanding of the method and an apparatus for carrying out the method will be obtained upon review of the detailed description set forth below when taken in conjunction with the accompanying drawing figures, which are briefly described as follows.

BRIEF DESCRIPTION OF THE DRAWINGS

FIG. 3 is a partially sectioned view of a controlled cavitation reactor for carrying out the method illustrating some of the interior components thereof.

DETAILED DESCRIPTION

A small volume cavitation reactor creates shockwaves that can open pores in biological material. This ability was demonstrated in oxygen delignification for the pulp and paper industry in which lignin was able to be effectively leached from the fibers without the use of oxygen. In conventional extraction, the raw material is heated in a reactor or vessel in the presence of a base at elevated temperatures and often is held in the vessel for hours or days. It has been discovered that, using a controlled cavitation reactor, the extraction of sugars, starches, and/or carbohydrates may be shortened to minutes and may produce higher extraction yields than with traditional batch extraction processes. This process may be especially useful for the extraction of sugars and starches from otherwise less productive products such as corn stover.

Figure 1:
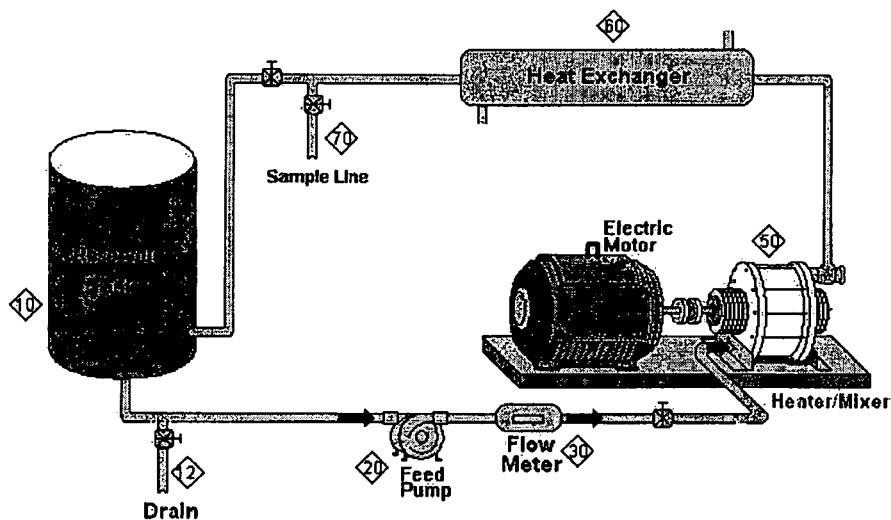
FIG. 1. Illustrates one embodiment of an apparatus for carrying out the method disclosed herein.

Referring to the drawing figures, FIG. 1 illustrates an apparatus for carrying out the extraction method of this invention. The apparatus includes a reservoir tank 10 for storing a mixture containing the sugar and starch bearing feed material, which may be grasses, corn, corn stover, or the like; water; and perhaps other materials designed to accelerate the extraction, such as an acid, a base, an enzyme, or combinations thereof. The mixture also may contain no accelerants and may just be a mixture of feed material and water. The mixture is drawn from the reservoir tank 10 by a feed pump 20 and pumped through a flow meter 30 and to a controlled cavitation reactor 50. Within the reactor 50, the mixture is exposed to cavitation and/or the resulting shockwaves and ultrasonic pressures. These shockwaves and pressures open the pores of the feed material and move liquids and any accelerants in the mixture into and out of the opened pores. This, in turn, liberates trapped sugars, starches, and/or carbohydrates from the feed material and these liberated substances become dissolved in the liquid within the mixture.

The mixture with dissolved liberated sugars and starches moves from the reactor 50 through a heat exchanger 60, where excess heat is removed from the mixture. The mixture then moves back to the reservoir tank 10. The contents of the reservoir tank 10 may be cycled through the reactor as described many times until a predetermined percentage of the sugars, starches, and/or carbohydrates has been removed from the feed material. Samples of the mixture may be removed through a sample line 70 and tested to determine when the maximum percentage has been removed. When the contents of the reservoir has been sufficiently treated, the reservoir, which now contains a liquid component rich in dissolved sugars, starches, and/or carbohydrates, may be removed through drain 12 for further processing into fuels such as ethanol.

The mixture itself may be from about 10 to about 50 wt % and more preferably from about 20 to about 30 wt % of feed material such as corn solids. Where accelerants or catalysts are used in the mixture, these substances may comprise from about 1 to about 12 wt % of the mixture. The remaining composition of the mixture may be water.

Figure 2:
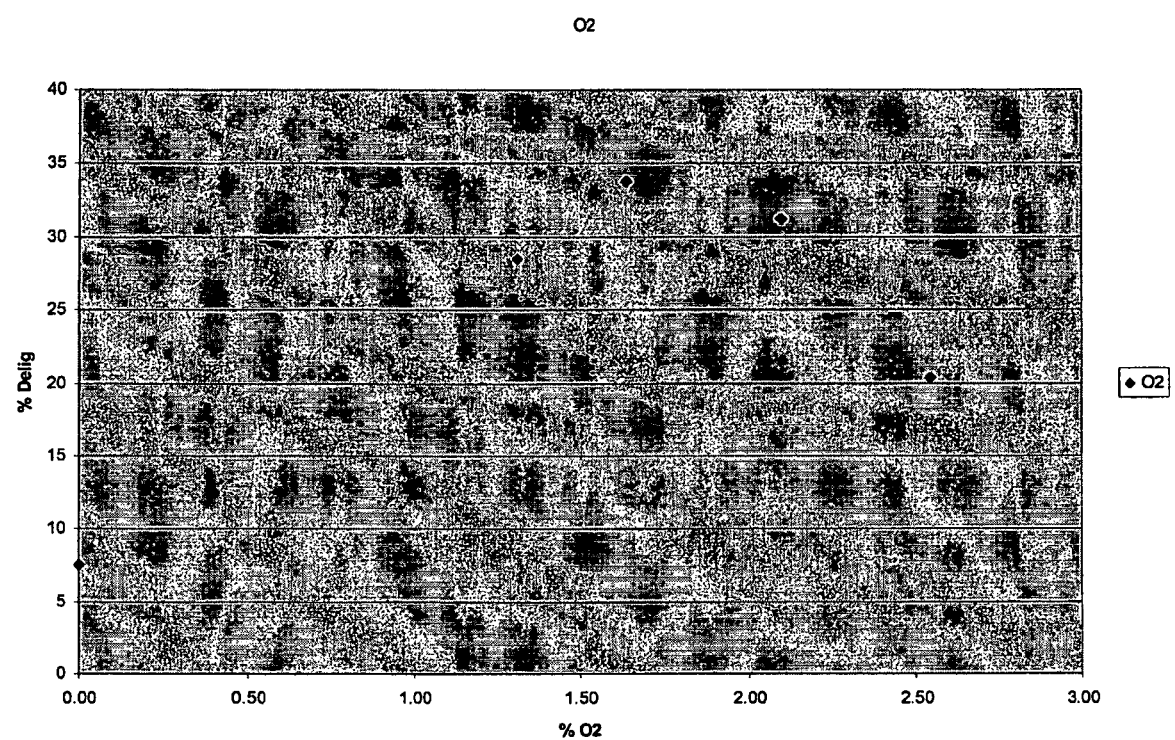
FIG. 2 is a chart illustrating the results of a test of the method and apparatus of this disclosure.

FIG. 2 is a graph showing the results of early tests of exposing lignocellulosic pulp to cavitation in an effort to remove lignin from the pulp. In these tests, a mixture of water, lignocellulosic pulp, and $O_2$ was exposed to cavitation within a controlled cavitation reactor. The test included one data point where no or 0% $O_2$ was added to the mixture. One would expect no lignin to be extracted under these circumstances. However, as is shown in the chart of FIG. 2, about 7 or 8 percent delignification occurred. Delignification is a multi-stage process. It was surmised that what had occurred to cause the observation was the removal of lignin that had been fragmented chemically in a previous stage, but that could not be removed by the standard agitated washing procedure followed by vacuum filtration. From these tests, it became clear that exposing the lignocellulosic material to cavitation and the resulting shockwave activity represented an improved and a more efficient method of removing lignin. It then occurred that, since corn and corn stover is somewhat similar to pulp fibers, a similar methodology might be transferred to the corn ethanol process to assist in getting enzymes into the corn or cellulosic ethanol structure and getting the chemically fragmented starches and sugars back out. The cavitation shockwave pressure fluctuations push and pull like a plunger on the pores of these natural substrates, which opens the pores and moves enzymes and other liquid materials in and out of the pores to liberate the trapped sugars, starches, and/or carbohydrates.

FIG. 3 is a partially cross sectioned view of a controlled cavitation reactor 11 similar but not identical to the reactor 50 of FIG. 1 and illustrating the process of the present disclosure. The reactor 11 comprises a housing 12 that defines a generally cylindrical interior chamber 15. The chamber 15 has a generally cylindrical peripheral wall and side walls. A cylindrical rotor 17 is mounted on a shaft 18 journaled in respective bearings 19 so that the rotor 17 is rotatable within the cylindrical chamber 15. The shaft 18 is driven by, for example, an electric motor (FIG. 1) to rotate or spin the rotor within the chamber. As can be seen in FIG. 3, the rotor 17 has a peripheral surface 26 that is spaced from the peripheral inner wall of the cylindrical chamber 15. This spacing defines a generally cylindrically-shaped zone that is referred to herein as the "cavitation zone." It should be understood, however, that the cavitation zone may or may not itself contain cavitation events. A plurality of bores 24 are formed in the peripheral surface of the rotor and are arranged in this illustration in two spaced rows extending around the circumference of the rotor. Inlets 30 are provided into the cylindrical chamber 17 and an outlet 33 is provided out of the chamber. In this embodiment, the inlets are located on the side walls of the housing and the outlet is located on the peripheral wall of the housing. It will be understood that other arrangements of inlets and outlets may be substituted, such as the arrangement illustrated in FIG. 1. In any event, a mixture 31 of water, feed material such as corn or corn stover, and/or an accelerant such as an acid, a base, a caustic, an enzyme, or otherwise, is feed to the chamber through the inlets 30. The inlets and outlets are arranged to ensure that the mixture traverses the cavitation zone before it is extracted from the chamber through the outlet 33. As the rotor is rotated rapidly in direction 23, cavitation events are generated within the bores 24 of the rotor. These cavitation events, in turn, create a cascade of shockwaves that radiate outwardly from the bores into the cavitation zone and through the mixture therein. The shockwaves successively and repeatedly bombard the feed material within the mixture imparting an ultrasonic "push and pull" effect of the surrounding liquid on the feed material. This, in turn, opens up the pores of the feed material and at the same time moves liquid and enzymes or another accelerant, if present, into and out of the pores. Trapped sugars, starches, and/or carbohydrates are thus liberated efficiently from the feed material and become dissolved in the surrounding liquid, from which they can be removed by traditional processes. Once treated, the mixture is pumped out the outlet and may be returned additional times if desired to remove a maximum amount of sugar, starch, and or carbohydrate from the feed material.

The invention has been described in terms of preferred embodiments and methodologies considered to represent the best mode of carrying out the invention. It will be understood, however, that various additions, deletions, and modifications might be made to the illustrated embodiments without departing from the spirit and scope of the invention as set forth in the claims.

What is claimed is:

1. A method of releasing carbohydrates from lignocellulosic biomass comprising the steps of:
   (a) mixing the lignocellulosic biomass with water to form a mixture;
   (b) moving the mixture through a controlled cavitation reactor to expose the mixture to shockwaves resulting from cavitation events so that the carbohydrates are released from the lignocellulosic biomass into the mixture to form a mixture containing dissolved carbohydrates; and
   (c) extracting the mixture containing dissolved carbohydrates from the controlled cavitation reactor.

2. The method of claim 1, wherein the controlled cavitation reactor includes a housing defining a cylindrical chamber, a cylindrical rotor rotatably mounted in the chamber, bores in a peripheral surface of the rotor, and a cavitation zone defined between the peripheral surface of the rotor and an interior wall of the chamber, the moving step comprising passing the mixture through the cavitation zone as the rotor rotates.

3. The method of claim 1, wherein the carbohydrates comprise at least one of sugars and starches.

4. The method of claim 1, wherein the lignocellulosic biomass comprises at least one of corn and corn stover.

5. The method of claim 1, wherein the lignocellulosic biomass comprises grass.

6. The method of claim 1, wherein the mixture in (a) comprises from about 10 to about 50 wt % lignocellulosic biomass.

7. The method of claim 1, wherein the mixture in (a) comprises from about 20 to about 30 wt % lignocellulosic biomass.

8. A method of releasing carbohydrates from pores of a lignocellulosic biomass, the method comprising the steps of:
   (a) mixing the lignocellulosic biomass with water to form a mixture;

(b) opening the pores of the lignocellulosic biomass, wherein opening the pores of the lignocellulosic biomass comprises moving the mixture through a cavitation zone of a controlled cavitation reactor to expose the mixture to shockwaves resulting from cavitation events, so that the carbohydrates are released into the mixture to form a mixture containing dissolved carbohydrates;

(c) moving the mixture containing dissolved carbohydrates out of the controlled cavitation reactor; and (d) separating the carbohydrates from the mixture containing dissolved carbohydrates.

9. The method of claim 8 further comprising moving the mixture containing dissolved carbohydrates through the cavitation zone of the controlled cavitation reactor at least an additional time before separating the carbohydrates from the mixture containing dissolved carbohydrates.

10. The method of claim 8, wherein the carbohydrates comprise at least one of sugars and starches.

11. The method of claim 8, wherein the lignocellulosic biomass comprises at least one of corn and corn stover.

12. The method of claim 8, wherein the lignocellulosic biomass comprises grass.

13. The method of claim 8, wherein the mixture in (a) comprises from about 10 to about 50 wt % lignocellulosic biomass.

14. The method of claim 8, wherein the mixture in (a) comprises from about 20 to about 30 wt % lignocellulosic biomass.

15. A method of extracting carbohydrates from lignocellulosic biomass and forming ethanol from the carbohydrates, the method comprising mixing the lignocellulosic biomass with water to form a mixture, exposing the mixture to shockwaves created by cavitation events to release the carbohydrates from the lignocellulosic biomass to form a mixture containing dissolved carbohydrates, extracting the carbohydrates from the mixture containing dissolved carbohydrates, and fermenting the extracted carbohydrates to form ethanol.

16. The method of claim 15, further comprising distilling the mixture containing ethanol to extract the ethanol.

17. The method of claim 15, wherein the lignocellulosic biomass comprises lignocellulosic biomass.

18. The method of claim 15, wherein the lignocellulosic biomass comprises at least one of corn and corn stover.

19. The method of claim 15, wherein the lignocellulosic biomass comprises grass.

20. The method of claim 15, wherein the mixture of lignocellulosic biomass and water comprises from about 10 to about 50 wt % lignocellulosic biomass.

21. The method of claim 15, wherein the mixture of lignocellulosic biomass and water comprises from about 20 to about 30 wt % lignocellulosic biomass.

* * * * *